United States Patent [19]

Mirza

[11] Patent Number: 5,366,465
[45] Date of Patent: Nov. 22, 1994

[54] ENDOSCOPIC SURGICAL PROCEDURE AND INSTRUMENT FOR IMPLEMENTATION THEREOF

[75] Inventor: M. Ather Mirza, 1 Piper La., St. James, N.Y. 11780

[73] Assignees: M. Ather Mirza, St. James; Theodor Esser, Stony Brook; Eugene T. King, East Northport, all of N.Y.

[21] Appl. No.: 16,048

[22] Filed: Feb. 10, 1993

Related U.S. Application Data

[63] Continuation of Ser. No. 986,523, Dec. 7, 1992.

[51] Int. Cl.⁵ .............................................. A61B 17/32
[52] U.S. Cl. .................... 606/170; 606/172; 128/898; 128/3
[58] Field of Search ............... 606/159, 170, 172; 604/22; 128/898, 3–11, 20

[56] References Cited

U.S. PATENT DOCUMENTS

| | | |
|---|---|---|
| 1,880,551 | 10/1932 | Wappler . |
| 4,497,320 | 2/1985 | Nicholson et al. . |
| 4,499,899 | 2/1985 | Lyons, III . |
| 4,512,344 | 4/1985 | Barber . |
| 4,610,242 | 9/1986 | Santangelo et al. . |
| 4,723,546 | 2/1988 | Zagorski . |
| 4,766,896 | 8/1988 | Pao . |
| 4,819,620 | 4/1989 | Okutsu . |
| 4,834,729 | 5/1989 | Sjostrom . |
| 4,877,026 | 10/1989 | de Laforcade . |
| 4,923,441 | 5/1990 | Shuler . |
| 4,962,770 | 10/1990 | Agee et al. . |
| 4,963,147 | 10/1990 | Agee et al. . |
| 4,969,450 | 11/1990 | Chinnock et al. . |
| 4,983,179 | 1/1991 | Sjostrom . |
| 4,986,825 | 1/1991 | Bays et al. . |
| 5,007,917 | 4/1991 | Evans . |
| 5,029,573 | 7/1991 | Chow . |
| 5,061,238 | 10/1991 | Shuler . |
| 5,089,000 | 2/1992 | Agee et al. . |
| 5,106,364 | 4/1992 | Hayafuji et al. . |

FOREIGN PATENT DOCUMENTS 2601802 7/1977 Germany ............................ 606/170

*Primary Examiner*—John D. Yasko
*Assistant Examiner*—Adam J. Cermak
*Attorney, Agent, or Firm*—Scully, Scott, Murphy & Presser

[57] ABSTRACT

A method of implementing an endoscopic surgical procedure on a patient, and more particularly, a novel and unique technique of performing a uniportal palmar subligmentous endoscopic carpal tunnel release. Moreover, also disclosed is a unique endoscopic surgical instrument adapted to be employed in the implementation of the foregoing method of endoscopically effecting the carpal tunnel release. This surgical procedure only requires the formation of a single and relatively small entry portal or incision in the palm proximate the distal side of the flexor retinaculum, thereby reducing any postoperative symptoms of the patient with only a cosmetically appealing scar formed on the palm, while eliminating the need for a second portal or incision proximate the wrist of the patient. Moreover, the endoscopic instrument employed in implementing the inventive method utilizes a unique cutting device which is mounted on a scope insertable through a cannula which has been initially inserted to extend beneath the flexor retinaculum from the distal side of the flexor retinaculum.

36 Claims, 3 Drawing Sheets

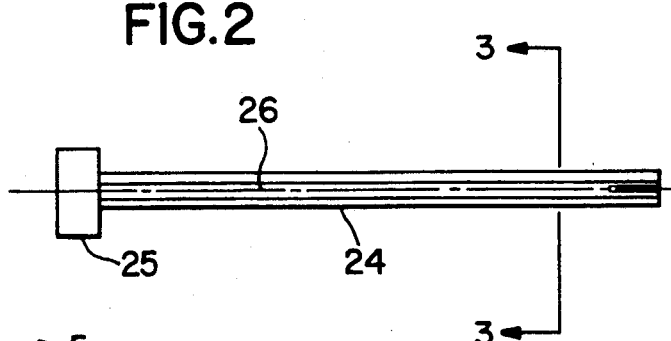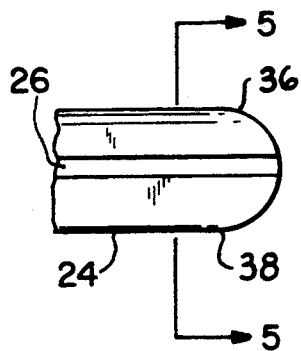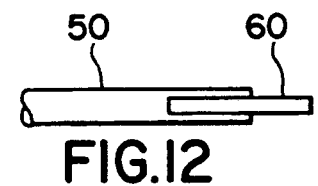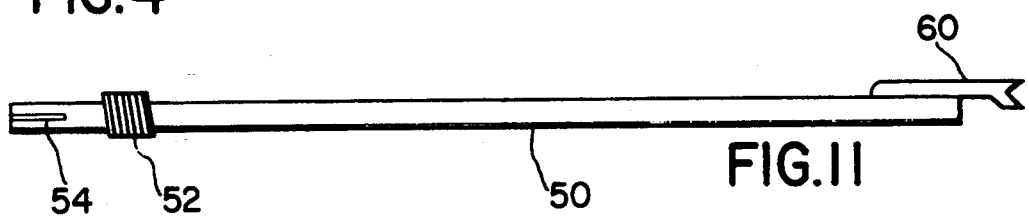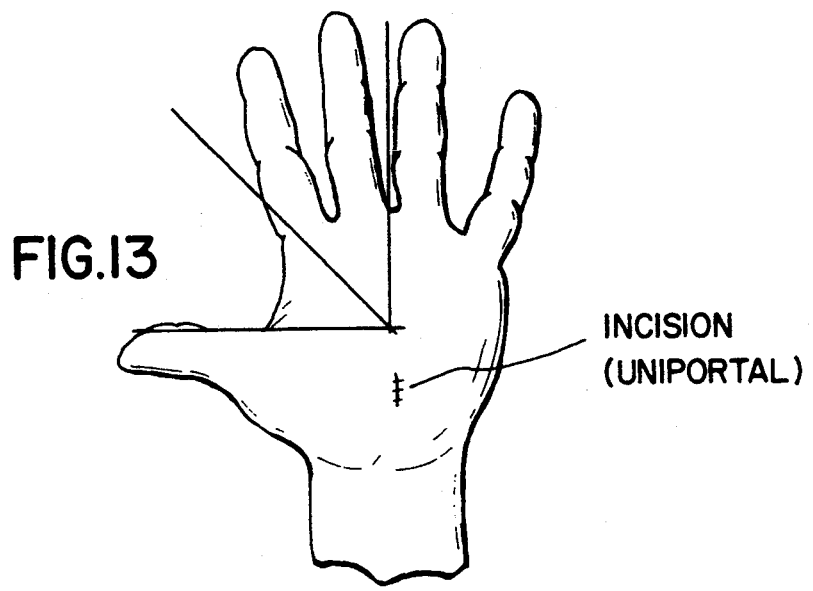

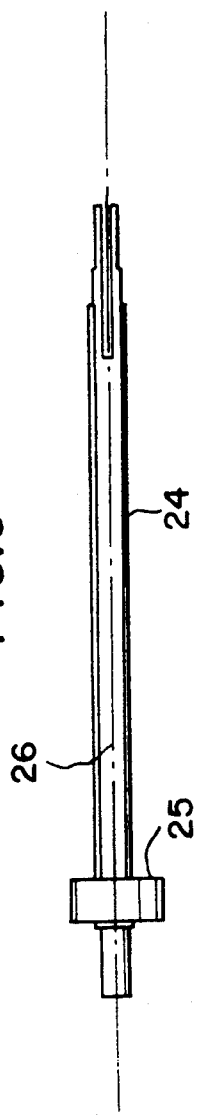
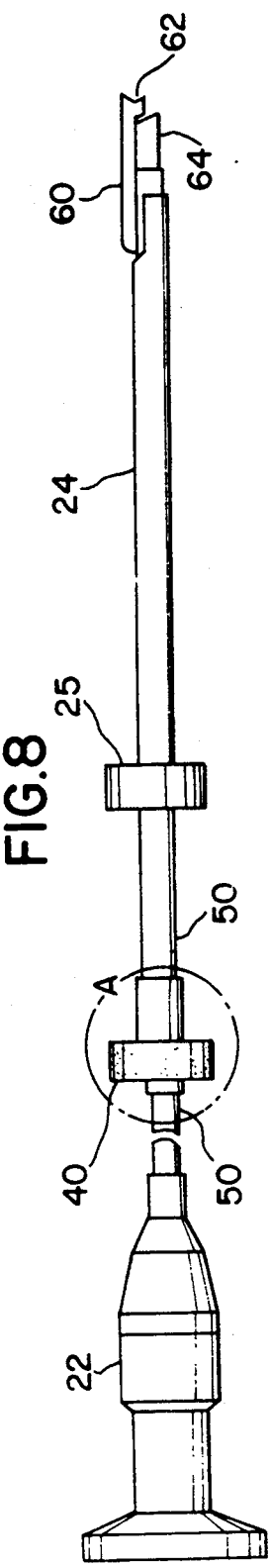
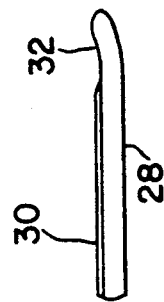
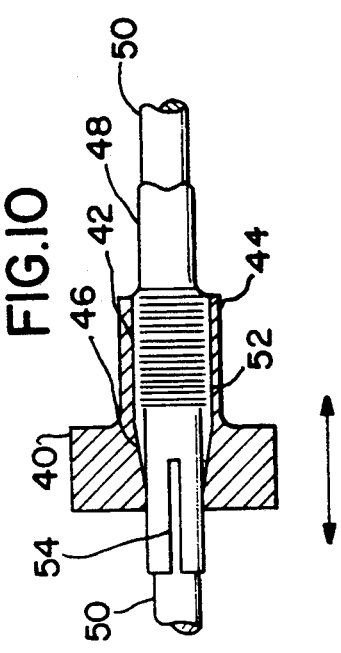

//<br>

ENDOSCOPIC SURGICAL PROCEDURE AND INSTRUMENT FOR IMPLEMENTATION THEREOF

CROSS-REFERENCE TO RELATED APPLICATION

This application is a continuation application of Ser. No. 07/986,523; filed Dec. 7, 1992.

BACKGROUND OF THE INVENTION

1. Field of the Invention

The present invention relates to a method of implementing an endoscopic surgical procedure on a patient, and more particularly, is directed to a novel and unique technique of performing a uniportal palmar subligmentous endoscopic carpal tunnel release. Moreover, the invention is also directed to the provision of a unique endoscopic surgical instrument adapted to be employed in the implementation of the foregoing method of endoscopically effecting the carpal tunnel release.

Carpal tunnel syndrome is a numbness in the thumb, index, middle and ring fingers resulting from pressure being exerted on the median nerve inside the carpal tunnel, interfering with the function of such median nerve. This may readily manifest itself as a pain radiating as far as the shoulders and neck of the patient, resulting in impaired grasping ability by the hand and loss of sleep. This physical phenomenon is the result of repetitive work and motions being carried out with the hand over lengthy periods of time, and is experienced by more ever younger people.

In essence, the carpal tunnel is formed by an arch of the eight wrist bones, spanned on its palmar surface by the transverse carpal ligament, the flexor retinaculum. The carpal tunnel functions as a large mechanical pulley to provide the appropriate moment arms for the digital flexor tendons as they pass through the tunnel. The tendons can then transmit force out into the fingers and impart only an appropriate amount of tension to develop torque at the level of the wrist.

Within the carpal tunnel, these tendons are lubricated and nourished by two synovial membranes—the radial and the ulnar bursa. The median nerve also shares the carpal tunnel, then branches out to provide sensory innervation to the palmar surfaces of the thumb, index, long and a portion of the ring finger. In addition, a small motor branch of the median nerve supplies the thenar muscles, which are responsible for lifting the thumb into opposition with the fingers.

Currently, a considerable array of methods or surgical techniques, and suitable therewith correlated surgical instruments, are being employed for purposes of implementing surgical procedures in effectuating carpal tunnel release in patients, and are generally designed for particular and highly specialized applications in this medical technology.

The customary procedure in implementing carpal tunnel release has heretofore been the forming of a lengthy incision, up to 8 cm in length across the palm from the wrist to the middle thereof, resulting in an unsightly scar, requiring division of all anatomical structures between the skin and the flexor retinaculum; i.e. the transverse carpal ligament. This created the potential for inadvertently cutting or injuring the palmar cutaneous nerve. Moreover, the patient normally encountered significant postoperative pain and discomfort, weakness of grip and pinch strength because of pillar infraction and the excessively lengthy extent of the incision. Such open surgery not only normally left the patient with a cosmetically unsightly scar extending from the wrist to the center of the palm, as mentioned hereinbefore, but also necessitated a lengthy and painful convalescence for the patient, whereby this convalescent period frequently caused the hand to be incapable of any significant physical work or manipulation for many weeks and even months, thereby effectively rendering the patient incapable of carrying out any meaningful work with the operated on hand and resulting in considerable financial losses being sustained by the patient.

Among more recent developments and advances in such surgical procedures, arthroscopic surgery employing the use of endoscopic devices has found widespread application, among others in connection with carpal tunnel release, in that in comparison with earlier customary surgical methods, any incisions necessary for such endoscopic/arthroscopic surgical procedures have been considerably reduced in size, thereby alleviating potential postoperative complications and pain encountered by the patient, while reducing any scarring to cosmetically desirable levels. Among various types of surgical procedures, techniques involving approaches by means of arthroscopic and endoscopic systems to carpal tunnel surgery have been acknowledged as being superior in providing significant advances over earlier so-called open surgical procedures necessitating large incisions. Such endoscopic surgical procedures have found widespread acceptance in effectuating carpal tunnel release for the purpose of alleviating the symptoms in a patient caused by carpal tunnel syndrome, also referred to as tardy median nerve palsy, normally caused by the compression of the median nerve within the carpal tunnel.

These more recent endoscopic surgical approaches to remedying varying types of surgical problems afforded desirable alternatives to such earlier open surgical procedures, and especially when applied to effectuating carpal tunnel release, have found widespread favor with surgeons and patients in comparison with the earlier surgical methods which primarily constituted complex open surgical procedures, and which involved lengthy and painful postoperative convalescent periods.

2. Discussion of the Prior Art

Among numerous publications which describe recent advances in endoscopic surgical methods and instruments employed in connection therewith, particularly such as may be employable for carpal tunnel release procedures, there may be found the Agee carpal tunnel release system as disclosed in Agee, et al. U.S. Pat. Nos. 4,963,147 and 5,089,000, both of which disclose endoscopic surgical instruments and surgical procedures implemented therewith, which when applied to carpal tunnel release through an effective severing of the flexor retinaculum, or transverse carpal ligament, are adapted to provide relief to the patient. However, the instrument and methods developed by Agee, et al. as described in those publications, although superior to open surgery, inhibit readily unobstructed visualization of the surgical site during the sequence of severing the flexor retinaculum and do not provide adequate control in the manipulation of the instrument so as to reduce the inherent danger of damage to surrounding nerves and tissue to an acceptable minimum, and additionally necessitate the forming of two entry portals or incisions in the wrist and hand. Moreover, the endoscopic instruments developed in Agee, et al. are relatively cumbersome and expensive, requiring the surgeon to always use both of his hands, and necessitate the use of a swivel cutting blade construction operable independently of a viewing scope, which does not always provide the appropriate visualization during cutting of the flexor retinaculum so as to potentially present the danger of causing damage to adjacent or contiguously located tissue or nerves relative to the operating site, which could lead to serious and possibly permanent injury to the patient.

Another surgical system and instrument providing for an advanced technique over Agee, et al., which is particularly adapted for carpal tunnel release through the intermediary of an endoscopic surgical procedure is disclosed in Chow U.S. Pat. No. 5,029,573. However, in that instance, although setting forth a considerable advance over the methodology disclosed in the Agee, et al. U.S. patents, the surgical procedure employed by Chow requires the formation of two entry and exit portals or incisions, one in the wrist area and one in the palm, and the passage of an endoscopic medical instrument, such as an obturator through a considerable length beneath the subcutaneous areas of the palm of the patient. Again, the necessity for two widely separated incisions or entry portals, and the requirement for inserting a scope from one end of the instrument from one portal and with the instrument extending outwardly from the other portal or incision, while surgically severing or cutting through the flexor retinaculum or transverse carpal ligament from the other portal or incision, engenders a considerable obstruction toward a clear nonproblematic visualization of the operating sate during the severing of the transverse carpal ligament and, once again, raises the specter of a potential risk of causing injury to tissue and nerves adjacent the operating site, especially such as to the median nerve, which could lead to serious permanent injury to a patient and possibly require additional corrective surgery necessitating subjecting the entire surgical or operating site to open surgery. Moreover, Agee, et al. and Chow require the surgeon to simultaneously employ both hands during the surgical procedures, thus necessitating the utilization of an unusually high degree of dexterity in manipulating the various components of the endoscopic surgical instruments.

SUMMARY OF THE INVENTION

The foregoing limitations and potential drawbacks which are encountered in the prior art publications are clearly and ambiguously obviated and improved upon through the inventive and novel method of implementing an endoscopic surgical procedure, and the unique and inventive endoscopic surgical instrument developed for accomplishing this purpose, especially for the effectuation of a carpal tunnel release; in essence, the severing of the flexor retinaculum or transverse carpal ligament through an endoscopic surgical procedure in which there is effected, by means of a uniportal or single incision, a palmar subligmentous endoscopic carpal tunnel release technique. This surgical procedure only requires the formation of a single and relatively small entry portal or incision in the palm proximate the distal side of the flexor retinaculum, thereby reducing any postoperative symptoms of the patient with only a cosmetically appealing scar formed on the palm, while eliminating the need for a second portal or incision proximate the wrist of the patient and concurrently avoiding injury to the palmar arch and branches of the median nerve. Moreover, the endoscopic instrument employed in implementing the inventive method utilizes a unique cutting device which is mounted on a scope insertable through a cannula which has been initially inserted to extend beneath the flexor retinaculum from the distal side of the flexor retinaculum or transverse carpal ligament, upon the formation of a passage beneath the flexor retinaculum, after hyperextending of the hand, by the preceding insertion and manipulation of a curved dissector. Thereafter, the dissector is removed and the cannula and an obturator which is contained therein are inserted through the incision into the previously formed passage beneath the flexor retinaculum. The cannula of the surgical instrument has the obturator withdrawn therefrom, and in place of the latter, a scope is inserted into the cannula which enables unhindered and unobstructed visualization of the operating site and of the flexor retinaculum.

The scope is then withdrawn from the cannula, and the same scope or another scope with a cutting blade mounted at the leading end thereof inserted into and advanced through the cannula towards the flexor retinaculum. Severing of the latter is then effected by the cutting blade while affording an unhindered view of the operating site through the scope, thereby resultingly dramatically reducing or even completely eliminating the risk of any injury being sustained by tissue and nerves in the vicinity of the operating site; for example, such as the median nerve. This particular unhindered visualization of the operating site also enables the surgeon to exercise an improved degree of control over the possibly single-handed manipulation of the endoscopic instrument and cutting blade.

Pursuant to a feature of the invention, the guiding member or cannula of the endoscopic instrument, and which contains the obturator which is initially employed to be advanced beneath the flexor retinaculum or transverse carpal ligament subsequent to withdrawal of the curved dissector, is provided with lateral or sideways wing-like or flange-like protrusions of curvilinear configurations which, in conjunction with an upwardly curving tip of the obturator projecting forwardly of the leading end of the cannula, is adapted to displace any tissue, or such as the media nerve, out of the path of the obturator and cannula as is being advanced; in effect, through essentially a sideways or lateral "shoving" action, thereby preventing any potential damage to such displaced tissue and nerve during the subsequent cutting procedure by maintaining such tissue well out of the way. Moreover, the leading tip of the obturator by being curved slightly upwardly towards the lower surface of the flexor retinaculum is also adapted to remove or dislocate any possible tissue or fascia located close to the surface of the flexor retinaculum and to ensure that the cannula and, resultingly, the subsequently inserted cutting blade are located as closely as possible to the flexor retinaculum.

The foregoing inventive concept ensures a simple and extremely efficient endoscopic surgical method which is particularly adapted, in conjunction with the use of the novel endoscopic instrument, for the implementation of a carpal tunnel release through the severing of the flexor retinaculum while producing minimal or no postoperative pain and discomfort in the patient, with a shortened convalescent period and with the formation only of a small cosmetically attractive scar on the palm of the patient's hand.

Accordingly, it is a primary object of the present invention to provide a novel and unique method of implementing an endoscopic surgical procedure through a uniportal entry to an operating site by a novel endoscopic surgical instrument.

The present invention has as a more specific object to provide an endoscopic surgical instrument with a novel scope-mounted cutting or blade element for implementing the endoscopic surgical procedure pursuant to the invention.

Still another object of the present invention is to provide an endoscopic surgical instrument of the type described, in which a scope which is adapted to be advanced through a cannula located beneath the flexor retinaculum has a cutting device mounted thereon to enable severing of the flexor retinaculum while being able to afford the surgeon an unobstructed visualization of the operating site, and avoiding damage or injury to the palmar arch and branches of the median nerve.

BRIEF DESCRIPTION OF THE DRAWINGS

Reference may now be had to the following detailed description of preferred embodiments of the endoscopic surgical instrument constructed pursuant to the invention, and to a surgical procedure for the effectuation of carpal ligament or tunnel release on a patient by a transverse severing of the flexor retinaculum, taken in conjunction with the accompanying drawings; in which:

FIG. 2 illustrates a longitudinal top view of a slotted cannula of the endoscopic surgical instrument pursuant to the invention;

FIG. 3 illustrates a sectional view taken along line 3—3 in FIG. 2;

FIG. 4 illustrates a top view of the leading end portion of a modified slotted cannula;

FIG. 5 illustrates a sectional view taken along line 5—5 in FIG. 4;

FIG. 6 illustrates a longitudinal side view of the leading end of an obturator adapted to be inserted into the slotted cannula of FIGS. 2 or 4;

FIG. 7 illustrates a top view of the leading end of the obturator;

FIG. 8 illustrates a longitudinal side view of the endoscopic instrument, showing the scope and cutting device mounted on the latter inserted into the slotted cannula;

FIG. 9 illustrates a top view of the leading section of the endoscopic instrument shown in FIG.

FIG. 10 illustrates, on a somewhat enlarged scale, a sectional view of the encircled portion 'A' of the instrument of FIG. 8;

FIG. 11 illustrates a longitudinal side view of a scope and cutting device or blade mounted thereon prior to the insertion thereof into the slotted cannula;

FIG. 12 illustrates a top view of the leading end portion of the scope and cutting device of FIG. 11; and FIG. 13 illustrates the palm portion of the hand of a patient showing the surgical markings applied thereto prior to implementing the incision for the carpal tunnel releasing surgery.

DETAILED DESCRIPTION

Figure 1:
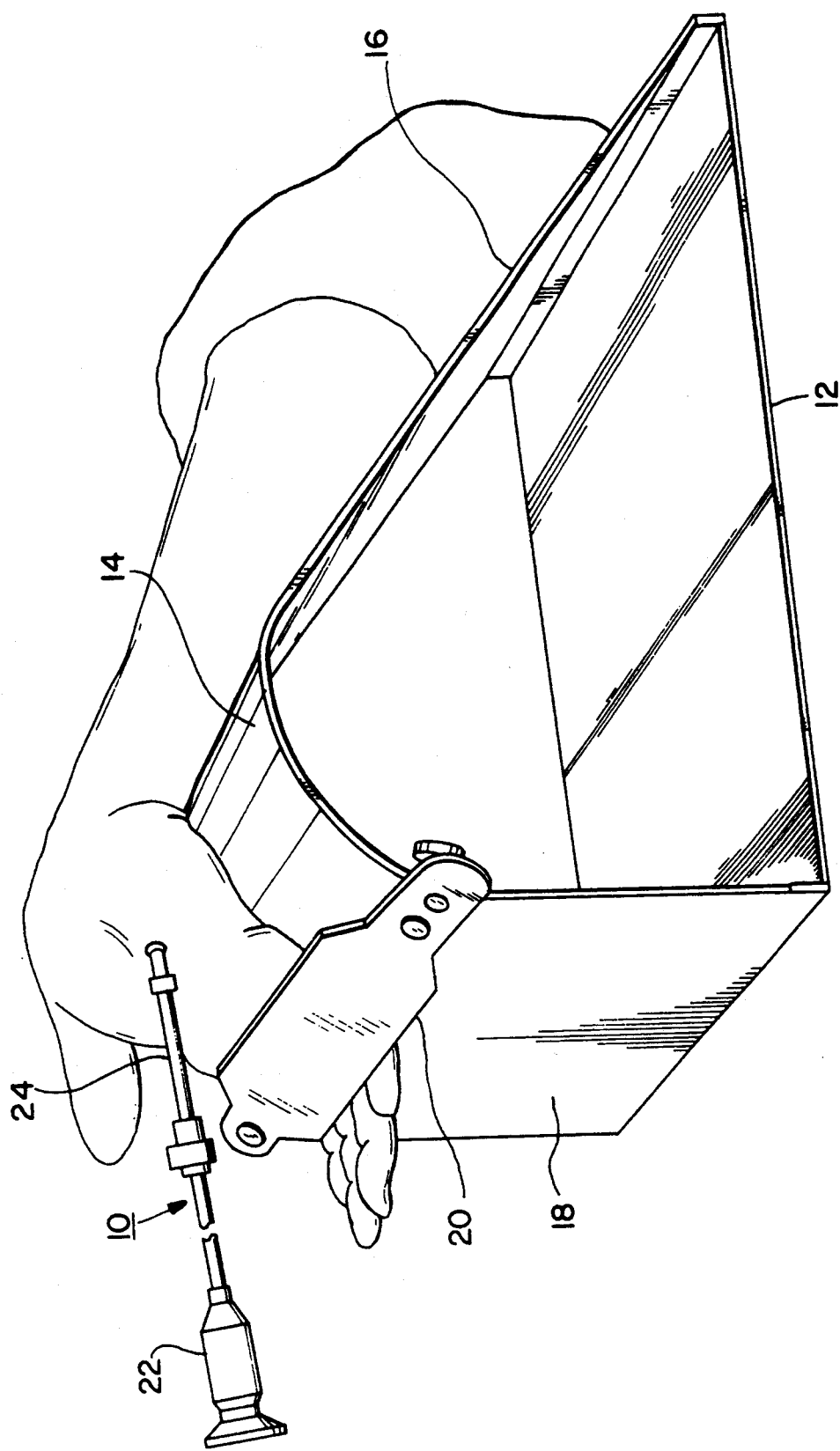
FIG. 1 illustrates a generally perspective view of the hand of the patient in a hyperextended position during a surgical procedure for effecting carpal ligament release, utilizing the endoscopic surgical instrument pursuant to the invention.

Reverting now in more specific detail to the description of the invention as represented by drawing FIGS. 1 through 12, FIG. 1 of the drawings illustrates an endoscopic system 10 employed for the procedure of effectuating the surgical release of a transverse carpal ligament; in essence, the severing of a flexor retinaculum in order to alleviate the symptoms and debilitating effects of carpal tunnel syndrome.

In this instance, the hand of a patient with the endoscopic system 10 is supported on a hand rest 12, which is in the form of a bolster having a curved upper surface 14 between an inclined or sloping surface 16 enabling the lower arm portion of a patient to be supported thereon, and a vertically depending front surface 18 with a strap 20 attached thereto for maintaining the hand of the patient in a hyperextended position in readiness for the endoscopic surgical procedure.

As shown in FIG. 1 of the drawings, the endoscopic instrument 10 which is to be utilized for effectuating the carpal ligament release; in effect, the severing or transverse cutting through of the flexor retinaculum, is shown in the operative position thereof inserted through an incision into the hand of a patient; with the surgical procedure being set forth in more specific detail hereinbelow.

Referring to FIGS. 1 through 11 of the drawings, and particularly FIGS. 2 through 10, the endoscopic surgical instrument 10 comprises an arthroscope 22 which includes a cannula 24 having a through extending longitudinal slot 26 formed therein, and a knob or flange-like member 25 at one end thereof, as shown specifically in FIGS. 2 and 3 of the drawing.

The knob or member 25, as shown in the drawings, has a central aperture which is sized to facilitate passage therethrough with sufficient clearance of any obturator, scope and cutting element which is to be inserted into and withdrawn from the cannula 24 and which projects through longitudinal slot 26, as described in detail hereinbelow.

An obturator 28, as in FIGS. 6 and 7, is adapted to be slidably received within the cannula, and presents a smooth outer surface through the intermediary of an axial, upstanding rib portion 30 which is engageable in close conformance within the longitudinal slot of the cannula upon insertion therein. The leading end of the obturator 28 is a tapered tip portion 32 which is bent upwardly in a direction towards the longitudinal rib to impart to the tip a somewhat upward curvature for a purpose to be described hereinbelow in more extensive detail.

Although the cannula 24, as shown in FIGS. 2 and 3, is illustrated as being circular in crosssectional configuration along its external surface, pursuant to a modified embodiment, as shown in FIGS. 4 and 5, at opposite sides of the longitudinal slot 26, the outer surface of the cannula 24 may be equipped with integrally formed outwardly extending curvilinear flange portions 36 and 38 so as to essentially form so-called wings or fins, as described further on hereinbelow. These fin-like wings or flange portions 36 and 38 are integrally formed with the cannula and are also curved so that upon insertion of the obturator into the cannula, the tip end of the obturator essentially forms a smooth curvature at its juncture with the flanges 36 and 38.

As shown more specifically in FIGS. 8 through 10, the endoscopic instrument 10 is illustrated in its condition for cutting through the flexor retinaculum to effectuate carpal tunnel or ligament release.

Hereby, the arthroscope 22 includes a suitable knurled knob 40 having an internal threaded portion 42 in a cylindrical extension 44 and a tapered bore 46 for receiving a tubular knife or cutting blade holder 48. The blade or knife holder 48 is adapted to receive a scope 50 of cylindrical configuration extending therethrough and lock the latter within the blade holder by simply axially displacing the knurled nut 40 through threaded interengagement between the internal thread 42 of the nut and an external thread 52 on the blade holder.

This will cause the tapered bore 46 of nut 40 to either compress the slotted portion 54 of the blade holder to clampingly engage the scope 50 or to loosen it so as to enable axial adjustment thereof relative to the blade holder.

A scope in the form of a rod member, in the absence of a blade holder, and which is connected to a video scanner (not shown) is adapted to be inserted through the cannula for effective visualization of the operative site.

The scope 50, at the leading end thereof includes a mounting for a cutting element, such as a flat knife blade 60 having a leading cutting edge 62, and with the scope 50 having a tapered or angled forward end surface 64 enabling light to be projected against the cutting device so as to illuminate the region of the operating site.

The knife blade 60 is adapted to be slid through the cannula 24 while mounted on the scope 50, after being advanced through the member 25, and with the knife blade 60 being afforded sufficient clearance to be inserted into and withdrawn through the member 25, so as to be slidingly engaged within the longitudinal slot 26 of the cannula during the forward advance thereof and while severing the flexor retinaculum. Moreover, the extent of forward advance of the knife blade in the cannula is readily controlled by adjusting the relative axial positioning of the scope within the tubular blade holder 48 and thereafter clamping the scope within the knife holder through activation of the knurled knob 40.

As shown in FIGS. 11 and 12 of the drawings, the cutting blade 60 may also be directly mounted on the holder 48 for the cylindrical scope 50, which has the distal end thereof provided with the external thread 52 which is engageable with the clamping nut 40, and with the slotted end portion 54 adapted to be tightened onto the scope.

The inventive endoscopic surgical procedure for effecting carpal tunnel release utilizing the novel uniportal palmar subligmentous endoscopic carpal tunnel release technique, and employing the novel endoscopic surgical instrument 10 is now described hereinbelow, by way of example.

Initially, after the hand is prepped, a regional anesthesia is applied to the hand of the patient which is to be subjected to the operative procedure. Thereafter, two lines are drawn, one transversely across the palm from the distal border of the thumb and another between the middle and ring fingers of the patient. At the point of intersection of the lines, and at a proximity of 1 cm thereto, a 1.5 cm long incision is made in the thenar crease or in a slight ulnar direction. The incision is deepened to expose the palmar fascia through the intermediary of blunt scissors in order to avoid injury to the palmar cutaneous branch of the median nerve. The distal edge of the flexor retinaculum is identified and divided for 5 to 6 mm approximately. Throughout this process, the palmar arch and the median nerve branches are protected. This palmar fascia is then divided longitudinally exposing the flexor retinaculum.

The hand is thereafter placed on the hand rest or bolster 12, with the forearm to which a tourniquet has been applied being supported on the inclined surface 16. The wrist is hyperextended in that the hand is positioned palm facing upwardly on the curved surface 14 with the fingers depending forwardly, and then clamped by means of the strap 20 to the bolster.

In this hyperextended position of the hand, a curved dissector is inserted through the incision so as to cause the posterior surface of the flexor retinaculum to be carefully dissected so as to peel the synovial tissue off the flexor retinaculum. Suitable retractors maintain the incision in an open spread condition. This enables the open incision or wound to be thoroughly irrigated.

Thereafter, the curved dissector is withdrawn, and the cannula 24 with the obturator 28 positioned therein with its tip 32 forwardly extended, is advanced into the incision along the path previously defined by the dissector in close proximity to the internal surface of the flexor retinaculum. This closeness is enhanced by the curvature imparted to the tip of the obturator.

Thereafter the obturator 28 is withdrawn while permitting the cannula 24 to remain in place beneath the flexor retinaculum, and a scope (without a cutting blade) is inserted through the cannula 24 to enable thorough visualization of the posterior surface of the flexor retinaculum. Hereby, it is important to be able to identify the flexor retinaculum endoscopically through the presence of its transversely oriented fibers. In the event that the scope ascertains that there is a presence of some synovial tissue obstructing the visualization of the transverse fibers, either a blunt dissector or a blunt hook may be employed to peel the thin and generally flimsy synovial lining away from the flexor retinaculum. Alternatively, if this particular presence of such tissue is of a substantial nature, the cannula 24 is withdrawn, the obturator repositioned therein, and the entire procedure repeated. This must be implemented until such time as the transverse fibers of the flexor retinaculum are clearly viewed endoscopically.

Upon the transverse fibers of the flexor retinaculum being clearly identified, the scope is then withdrawn from the cannula 24, and the scope 50 having the cutting device, consisting of the blade 60 mounted thereon, is inserted through the cannula 24 and advanced towards the operating site represented by the transverse carpal ligament or flexor retinaculum. The angled leading end 64 of the scope 50 on which the cutting blade 60 is mounted enables projection of illuminating light against the blade and the surrounding regions of the operating site so as to constantly afford direct unobstructed visualization of the operative region during the carpal ligament releasing procedure.

As the scope and the cutting device or blade 60 mounted thereon is advanced, the cutting edge 62 of the latter will divide the flexor retinaculum throughout its transverse width while being maintained under endoscopic visualization. Upon completion of the severing of the flexor retinaculum, the scope 50 and the thereon mounted cutting blade 60 are withdrawn from the cannula, and a scope without a cutting device thereon is reinserted into the cannula to provide for a viewing of the cut edges of the flexor retinaculum so as to ensure the complete division thereof has been accomplished. Once the intactness of the media nerve and surrounding structures have been verified through suitable rotation of the cannula about its longitudinal axis so as to afford a broader overview, the entire endoscopic surgical instrument 10 is withdrawn from the operating site out of the incision.

Prior to closing and suturing the incision, the wound is again inspected; on the one hand, by direct visualization of the cut edges of the flexor retinaculum, and one the other hand, by inserting the blunt dissector to assess the length and completeness of the division of the flexor retinaculum. The wound is then irrigated and sutured, with a tincture of benzoin applied thereto, thereafter applying a steristrip and the hand placed in a soft fluff dressing.

From the foregoing, it becomes readily apparent that the inventive surgical procedure, employing only a uniportal or single incision enables the operation to be implemented much more rapidly than heretofore, while forming only a cosmetically attractive small single scar in the palm, while extensively reducing the postoperative recovering period of the patients. In at least one-third of the patients, no pain was experienced postoperatively, obviating the necessity for any medication in effect, one-third of the patients did no require medical care.

Moreover, the average length of time postoperatively for being able to gainfully utilize the hand and, thereby to return to work, was approximately 14 days, with executives normally being able to return to work at about 7 days subsequent to the operation, clerical/secretarial staff at approximately 17 days, and workers involved in heavy physical labor at approximately 28 days after surgery.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A method of implementing an endoscopic surgical procedure at a selected operative site on a patient; comprising the steps of:

making an incision on said patient at a locale proximate said operative site to establish an entry portal;

inserting an elongate insertion member into a longitudinal bore of an elongate cannular guide member having open proximal and distal ends and an open slot extending along the length thereof communicating with said open ends, said elongate insertion member being slidably receivable within said cannular guide member and being configured so that at least portions thereof conform with said open distal end and said open slot of the guide member to form a smooth exterior surface in combination therewith;

introducing a leading end of the combination of said cannular guide member and the therein inserted insertion member into said entry portal and advancing said combination a predetermined distance relative to said operative site;

withdrawing said insertion member while permitting said cannular guide member to remain in place at said operative site;

inserting endoscopic viewing means into said cannular guide member for direct visualization of said operative site and the positioning of said guide member relative to said site;

withdrawing said endoscopic viewing means from said cannular guide member;

mounting a surgical instrument on further endoscopic viewing means proximate the leading end of said further viewing means;

inserting said composite further endoscopic viewing means and surgical instrument into said cannular guide member such that the surgical instrument protrudes into the open slot in said cannular guide member, and advancing said composite endoscopic viewing means and surgical instrument so as to contact tissue at said operative site with said surgical instrument;

operatively engaging said tissue with said surgical instrument while advancing the latter under direct visualization through said further endoscopic viewing means so as to perform a desired operative procedure on said tissue;

withdrawing said composite further endoscopic viewing means and surgical instrument from said cannular guide member;

withdrawing said cannular guide member through said entry portal and suturing said incision.

2. A method as claimed in claim 1, wherein said surgical instrument comprises cutting means for severing tissue at said operative site.

3. A method as claimed in claim 2, wherein said cutting means comprises a blade member having a leading cutting edge for severing tissue responsive to advancing said further endoscopic viewing means forwardly within said cannular guide member.

4. A method as claimed in claim 3, wherein said open slot in said cannular guide member has the opposite said edges thereof forming guide surfaces for said blade member inhibiting rotation of said blade about the longitudinal axis of said cannular guide member.

5. A method as claimed in claim 3, wherein the leading end of said further endoscopic viewing means includes an angled surface facing said blade member for directing illuminating light against the blade member and towards the region of the operating site proximate at least the cutting edge of said blade member.

6. A method as claimed in claim 2, wherein said surgical procedure is a uniportal palmar subligmentous carpal tunnel release, wherein an incision forming said entry portal comprises cutting skin, subcutaneous tissue and fascia is located proximate one edge of the transverse carpal ligament, said combination of insertion member and cannular guide member being inserted through said incision and advanced beneath said transverse carpal ligament towards the opposite edge thereof and in close surface proximity therewith.

7. A method as claimed in claim 6, wherein said cutting means is adapted to sever said transverse carpal ligament so as to provide for a carpal tunnel release.

8. A method as claimed in claim 6, wherein said cannular guide member includes external structure for displacing the palmar cutaneous branch of the median nerve during advance thereof beneath said transverse carpal ligaments so as to prevent any damage to the nerve.

9. A method as claimed in claim 8, wherein said external structure comprises flange-like protrusions arranged on opposite sides of the open slot in said cannular guide member.

10. A method as claimed in claim 1, wherein said insertion member comprises an obturator.

11. A method as claimed in claim 6, wherein said obturator has a tapered leading tip portion.

12. A method as claimed in claim 7, wherein said tapered leading tip portion of the obturator includes a curvature so as to angle the tip portion towards the plane of the cannular guide member possessing the open slot.

13. A method as claimed in claim 1, wherein means provide for adjustable limits in advancing said composite further viewing means and surgical instrument within said cannular guide member relative to said operative site.

14. A method as claimed in claim 1, wherein said incision at said locale is placed to avoid injury to the palmar cutaneous branch of the median nerve.

15. An instrument for implementing an endoscopic surgical procedure at a selected operative site on a patient through an incision on said patient at a locale proximate said operative site to establish an entry portal; said instrument comprising an elongate cannula guide member including a longitudinal bore having open proximal and distal ends and an open slot extending along the length thereof communicating with said open ends; an elongate insertion member being slidably receivable within said cannula guide member and being configured so that at least portions thereof conform with said open distal end and said open slot of the guide member to form a smooth exterior surface in combination therewith, said cannula guide member and the inserted insertion member being advanceable a predetermined distance relative to said operative site, said insertion member being sized for withdrawal from said cannula guide member while permitting said cannula guide member to remain in place at said operative site; endoscopic viewing means being inserted into said cannula guide member for direct visualization of said operative site and the positioning of said cannula guide member relative thereto and thereafter sized for withdrawal from said cannula guide member;

a further endoscopic viewing means; a surgical instrument being mounted proximate a leading end of said further viewing means;

said cannula guide member being sized to provide clearance for said composite further endoscopic viewing means and surgical instrument which is to be inserted into and passed through said cannula guide member such that the surgical instrument protrudes through the open slot in said cannula guide member to advance said composite further endoscopic viewing means and surgical instrument so as to contact tissue at said operative site with said surgical instrument, said tissue being operatively engageable with said surgical instrument under direct visualization through said further endoscopic viewing means so as to perform a desired operative procedure on said tissue, said composite further endoscopic viewing means and surgical instrument being sized for withdrawal from said cannula guide member, and said guide member being sized for withdrawal from said entry portal.

16. An instrument as claimed in claim 15, wherein said surgical instrument comprises cutting means for severing tissue at said operative site.

17. An instrument as claimed in claim 16, wherein said cutting means comprises a blade member having a leading cutting edge for severing tissue responsive to advancing said further endoscopic viewing means forwardly within said cannular guide member.

18. An instrument as claimed in claim 17, wherein said open slot in said cannular guide member has opposite side edges thereof forming guide surfaces for said blade member inhibiting rotation of said blade member about the longitudinal axis of said cannular guide member.

19. An instrument as claimed in claim 17, wherein the leading end of said further endoscopic viewing means includes an angled surface facing said blade member for directing illuminating light against the blade member and towards the region of the operating site proximate at least the cutting edge of said blade member.

20. An instrument as claimed in claim 16, wherein said combination of further insertion member comprising said further endoscopic viewing means and surgical instrument and cannula guide member is sized for insertion through said incision and advanced beneath the transverse carpal ligament towards the opposite edge of and positioned in close surface proximity with the ligament to implement a surgical procedure of a uniportal palmar subligmentous carpal tunnel release, wherein said incision forming said entry portal comprises cutting skin, subcutaneous tissue and fascia is located proximate one edge of the transverse carpal ligament.

21. An instrument as claimed in claim 20, wherein said cutting means comprises a cutting blade for severing said transverse carpal ligament so as to provide for a carpal tunnel release.

22. An instrument as claimed in claim 20, wherein said cannular guide member includes external structure for displacing the palmar cutaneous branch of the median nerve during advance thereof beneath said transverse carpal ligaments so as to prevent any damage to the median nerve.

23. An instrument as claimed in claim 22, wherein said external structure comprises laterally extending protrusions arranged on opposite sides of the open slot in said cannular guide member.

24. An instrument as claimed in claim 15, wherein said insertion member comprises an obturator.

25. An instrument as claimed in claim 24, wherein said obturator has a tapered leading tip portion.

26. An instrument as claimed in claim 25, wherein said tapered leading tip portion of the obturator includes a curvature so as to angle the tip portion towards the open slot formed in the cannula guide member.

27. An instrument as claimed in claim 15, wherein means limit the extent of advance of said composite further viewing means and surgical instrument within said cannular guide member relative to the operating site.

28. An instrument as claimed in claim 27, wherein said limiting means comprise a mounting sleeve for said further viewing means; and rotatably and axially movable means for selectively causing said mounting sleeve to clampingly engage or release said further viewing means to enable axial adjustment thereof in said mounting sleeve.

29. An apparatus as claimed in claim 28, wherein said movable means comprises; a nut an internal screwthread formed in said nut; an external screwthread formed on said mounting sleeve, said internal screwthread cooperatively engaging said external screwthread, and axial extension means on said nut having an internal tapered surface for releasably clamping said mounting sleeve responsive to rotation of said nut in a predetermined rotational direction.

30. An apparatus as claimed in claim 29, wherein said nut has a knurled external circumferential surface to facilitate manipulation thereof.

31. An instrument as claimed in claim 15, wherein said incision at said locale is placed to avoid injury to the palmar cutaneous branch of the median nerve.

32. A method of implementing an endoscopic surgical procedure at a selected operative site on a patient; wherein said surgical procedure is a uniportal palmar subligmentous carpal tunnel release, wherein an incision forming said entry portal comprising cutting skin, subcutaneous tissue and fascia is located proximate one edge of the transverse carpal ligament, comprising the steps of:

inserting an elongate insertion member into a longitudinal bore of an elongate cannula guide member having open proximal and distal ends and an open slot extending along the length thereof communicating with said open ends, said elongate insertion member being slidably receivable within said cannula guide member and being configured so that at least portions thereof conform with said open distal end and said open slot of the guide member to form a smooth exterior surface in combination therewith;

introducing a leading end of the combination of said cannula guide member and the therein inserted insertion member into said entry portal and advancing said combination a predetermined distance relative to said operative site;

withdrawing said insertion member while permitting said cannula guide member to remain in place at said operative site;

inserting endoscopic viewing means into said cannula guide member for direct visualization of said operative site and the positioning of said guide member relative to said site;

withdrawing said endoscopic viewing means from said cannula guide member;

mounting a surgical instrument on further endoscopic viewing means proximate the leading end of said viewing means;

inserting said composite further endoscopic viewing means and surgical instrument into said cannula guide member such that the surgical instrument protrudes into the open slot in said cannula guide member, and advancing said composite endoscopic viewing means and surgical instrument so as to contact tissue at said operative site with said surgical instrument, and operatively engaging said tissue with said surgical instrument while advancing the latter under direct visualization through said further endoscopic viewing means so as to perform a desired operative procedure on said tissue.

33. A method as claimed in claim 32, comprising the steps of:

withdrawing said composite further endoscopic viewing means and surgical instrument from said cannula guide member; and withdrawing said cannula guide member through said entry portal and suturing said incision.

34. A method as claimed in claim 32, wherein tissue is severed by said surgical instrument at said operative site.

35. A method as claimed in claim 32, wherein said surgical instrument severs tissue responsive to advancing said further endoscopic viewing means forwardly within said cannula guide member.

36. A method as claimed in claim 32, wherein said cannula guide member displaces the palmar cutaneous branch of the median nerve during advance thereof beneath said transverse carpal ligaments so as to prevent any damage to the nerve.

* * * * *

UNITED STATES PATENT AND TRADEMARK OFFICE
CERTIFICATE OF CORRECTION

PATENT NO. : 5,366,465
DATED : November 22, 1994
INVENTOR(S) : M. A. Mirza

It is certified that error appears in the above-indentified patent and that said Letters Patent is hereby corrected as shown below:

Column 3, line 34: "sate" should read --site--
Column 5, line 56: after "FIG." insert --8;--
Column 6, line 54: "crosssectional" should read --cross-sectional--
Column 9, line 8: "one" should read --on--
Column 9, line 25: "no" should read --not--

Column 11, line 5, Claim 11: "claim 6" should read --claim 10--
Column 11, line 7, Claim 12: "claim 7" should read --claim 11--

Signed and Sealed this

Twenty-third Day of May, 1995

Attest:

BRUCE LEHMAN

*Attesting Officer*        *Commissioner of Patents and Trademarks*